United States Patent [19]
Hochstedler et al.

[11] Patent Number: 6,004,288
[45] Date of Patent: Dec. 21, 1999

[54] BREAST PUMP

[76] Inventors: Judy R. Hochstedler; Curtis G. Hochstedler, both of 200 Pond Pine St., Tallahassee, Fla. 32310

[21] Appl. No.: 09/198,840

[22] Filed: Nov. 24, 1998

[51] Int. Cl.⁶ .................................................. A61M 1/06
[52] U.S. Cl. .............................................. 604/74; 417/474
[58] Field of Search ................ 604/73, 74, 118, 604/119, 313–316, 327, 346, 355, 540; 119/14.07, 14.23, 14.31, 14.37, 14.38, 14.42, 14.52, 14.54; 417/474

[56] References Cited

U.S. PATENT DOCUMENTS

| | | | |
|---|---|---|---|
| 4,964,851 | 10/1990 | Larsson | 604/74 |
| 5,295,957 | 3/1994 | Aida et al. | 604/74 |
| 5,720,722 | 2/1998 | Lockridge | 604/74 |
| 5,810,772 | 9/1998 | Niederberger | 604/74 |
| 5,947,923 | 9/1999 | Uehara et al. | 604/74 |

*Primary Examiner*—Wynn Wood Coggins
*Assistant Examiner*—Eric Kline
*Attorney, Agent, or Firm*—Peter Loffler

[57] ABSTRACT

A breast pump that gently milks a lactating mother's breast is comprised of a housing having a flexible sleeve that receives the breast. A rotating wheel and connection rod combine to reciprocate the sleeve back and fourth relative to an opening on the housing while a cam operates to squeeze and unsqueeze the sleeve. A motor operatively connects to the cam and to the wheel. An adjustment mechanism adjusts the initial parameters of the sleeve in order to accommodate various sized breasts.

20 Claims, 6 Drawing Sheets

BREAST PUMP

BACKGROUND OF THE INVENTION

1. Field of the Invention

The present invention relates to a hand held breast pump.

2. Background of the Prior Art

Breast pumps for pumping milk from a lactating mother for delivery to a child are well known in the art. U.S. Pat. No. 5,601,531 to Silver, U.S. Pat. No. 5,571,084 to Palmer, U.S. Pat. No. 4,759,747 to Aida et al., U.S. Pat. No. 4,323,067 to Adams, and U.S. Pat. No. 2,542,505 to Gascoigne are all examples of such devices. While these and other breast pumps found in the art work with varying degrees of efficiency, they suffer from one or more problems.

Many devices are unduly complex in design, making them expensive to manufacture and maintain. Other devices are relatively complex and difficult to operate, making their use by a mother less attractive. Still other devices cause discomfort and pain, making their use by a mother very unattractive.

Therefore, there is a need in the art for a breast pump that overcomes the problems associated with current state of the art devices. Such a breast pump must be of relatively simple design and construction and must be easy to use. Use of the breast pump must not result in unde pain or discomfort to the user.

SUMMARY OF THE INVENTION

The breast pump of the present invention addresses the aforementioned needs in the art. The breast pump is of a relatively simple design and is constructed using standard manufacturing techniques. Hookup and operation of the device is relatively straightforward. A mother using the device will not experience undue discomfort or pain.

The breast pump of the present invention is comprised of a housing having a first opening, a second opening and a flexible sleeve, with a first side and a second side having a third opening, disposed therein. Rollers are provided on each of the sides of the sleeve. A tube extends from the first opening, passes through the third opening and terminates proximate a receptacle removably attached to the housing at the second opening. A connection rod has one end pivotally attached to the housing and an opposing end pivotally attached to the sleeve and has a slotted portion. A wheel is rotatably disposed within the housing and has a post secured therein in offset relation to the center of the wheel, the post being received within the slotted portion. A cam is reciprocatively disposed within the housing and engages the sleeve, either directly or by way of a flange. A motor assembly powered by a motor, is operatively connected to the wheel and to the cam. In operation, the wheel and connection rod act to reciprocate the sleeve back and forth relative to the first opening and thereby produce a pulling action on the breast received through the first opening, while the cam acts on the sleeve to compress and release the sleeve thereby producing a squeezing action upon the breast. A roller acts on the sleeve to adjust the initial width created between the two sides of the sleeve. The roller is adjustable by way of a spring having one end biased against the roller and an opposing end biased against a knob rotatably disposed within the housing. Rotation of the knob brings the two sides of the sleeve closer together while counterrotation of the knob allows the two sides to move farther apart from each other.

BRIEF DESCRIPTION OF THE DRAWINGS

Similar reference numerals refer to similar parts throughout the several views of the drawings.

DESCRIPTION OF THE PREFERRED EMBODIMENT

Figure 1:
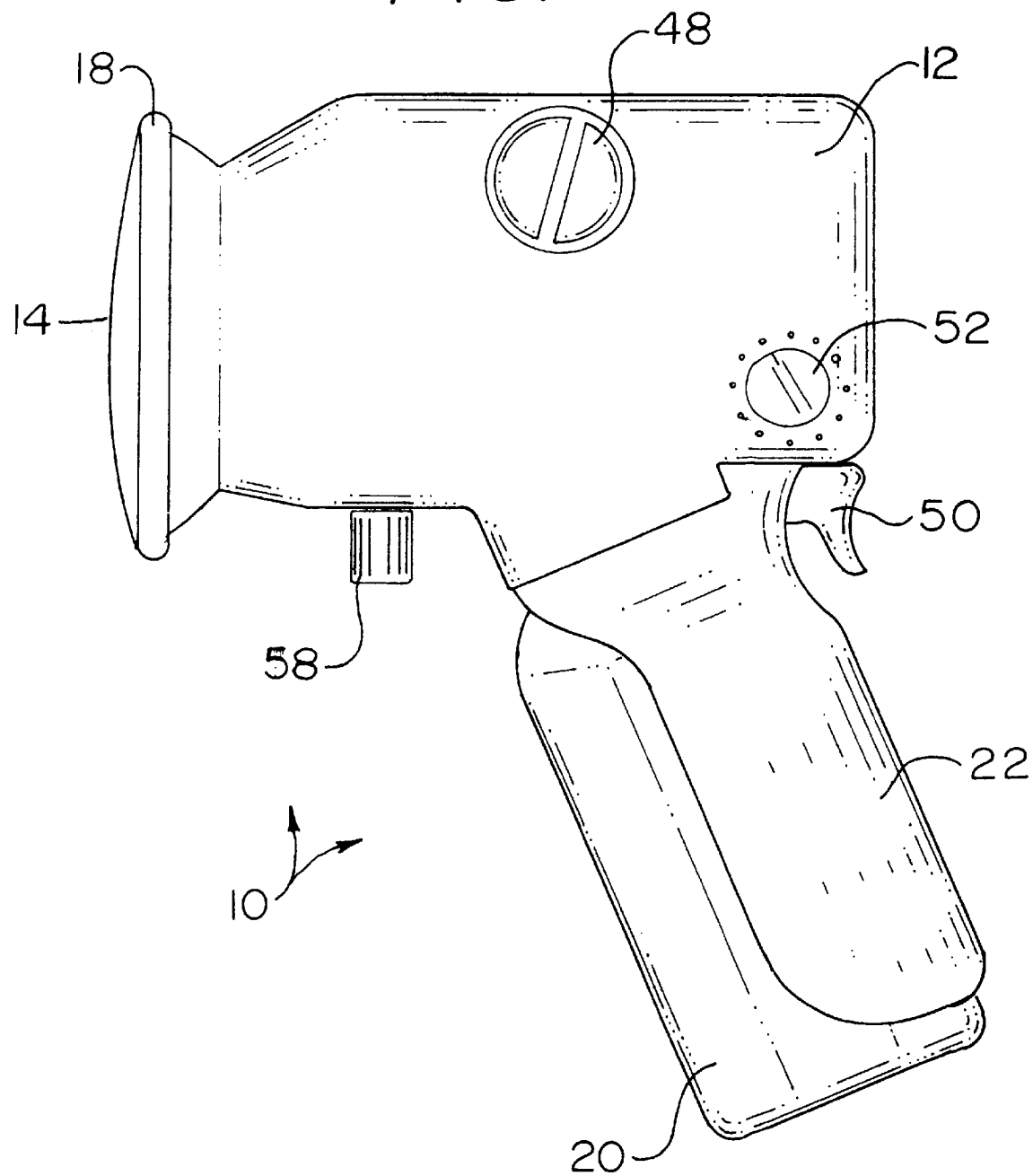
FIG. 1 is a side elevation view of the breast pump of the present invention.
Figure 2:
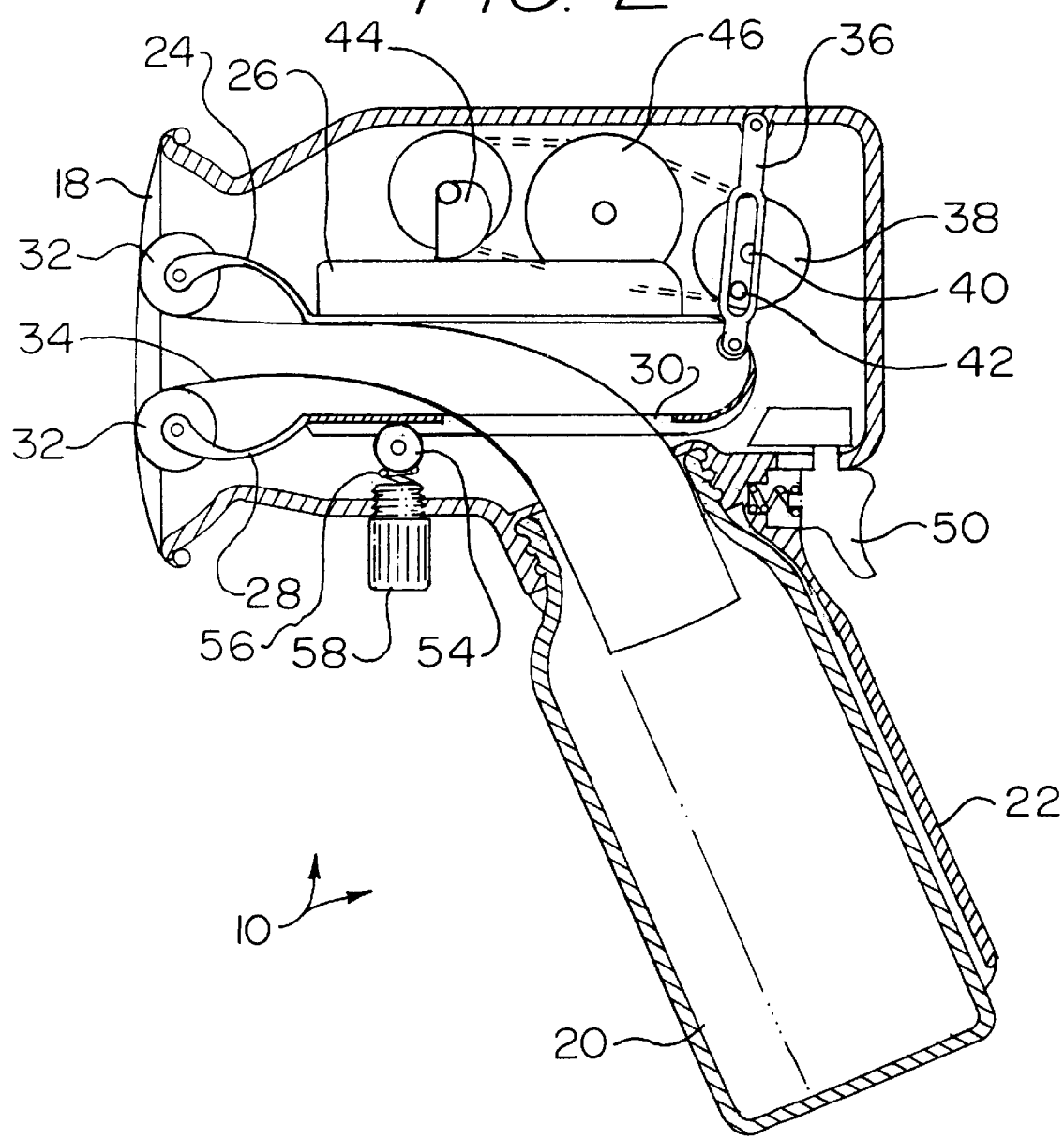
FIG. 2 is a side sectioned view of the breast pump.
Figure 3:
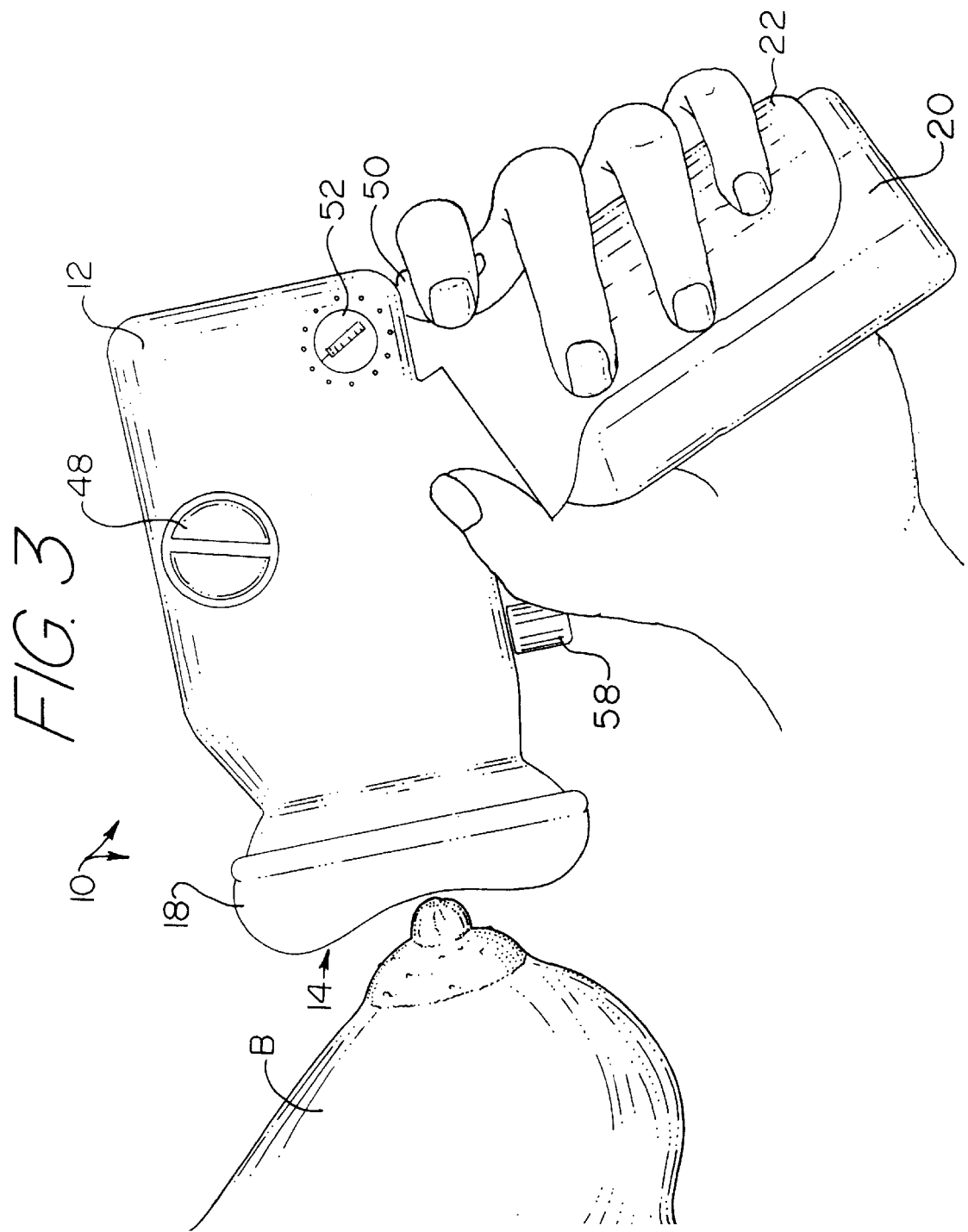
FIG. 3 is a side elevation view of the breast pump receiving a breast.
Figure 4:
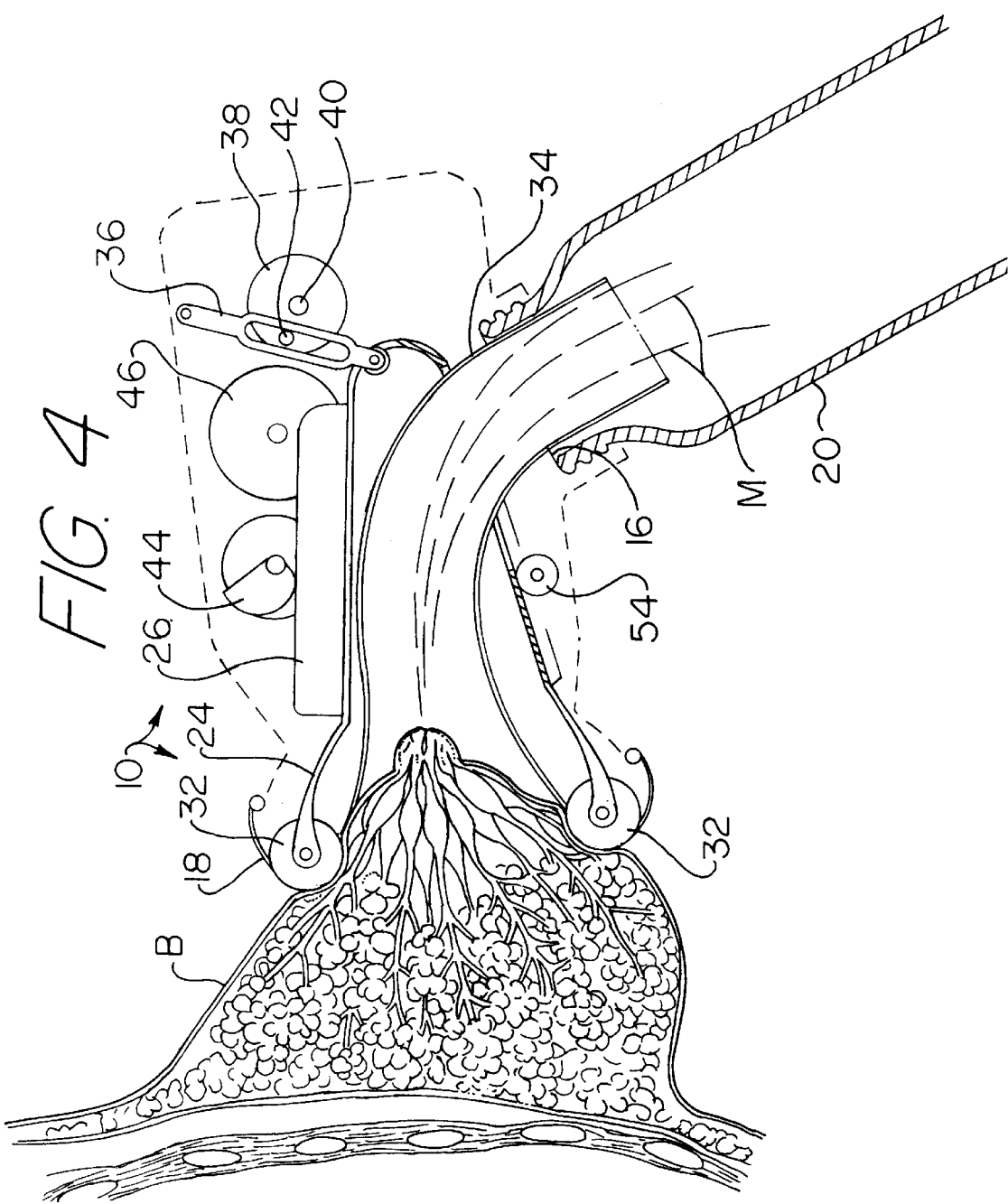
FIG. 4 is a sectioned view of the breast pump with the sleeve in a forward unsqueezed position.
Figure 5:
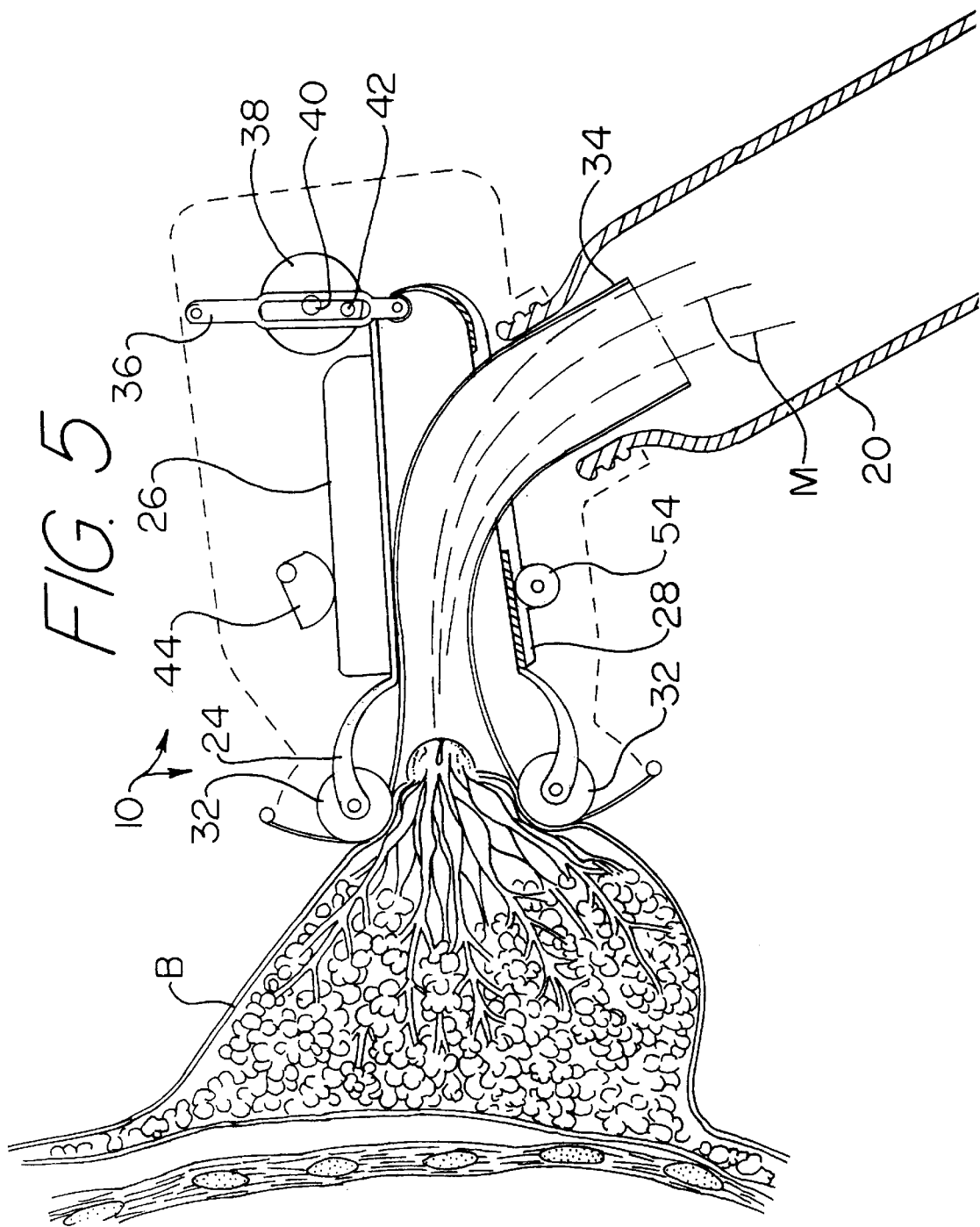
FIG. 5 is a sectioned view of the breast pump with the sleeve in a middle partially squeezed position.
Figure 6:
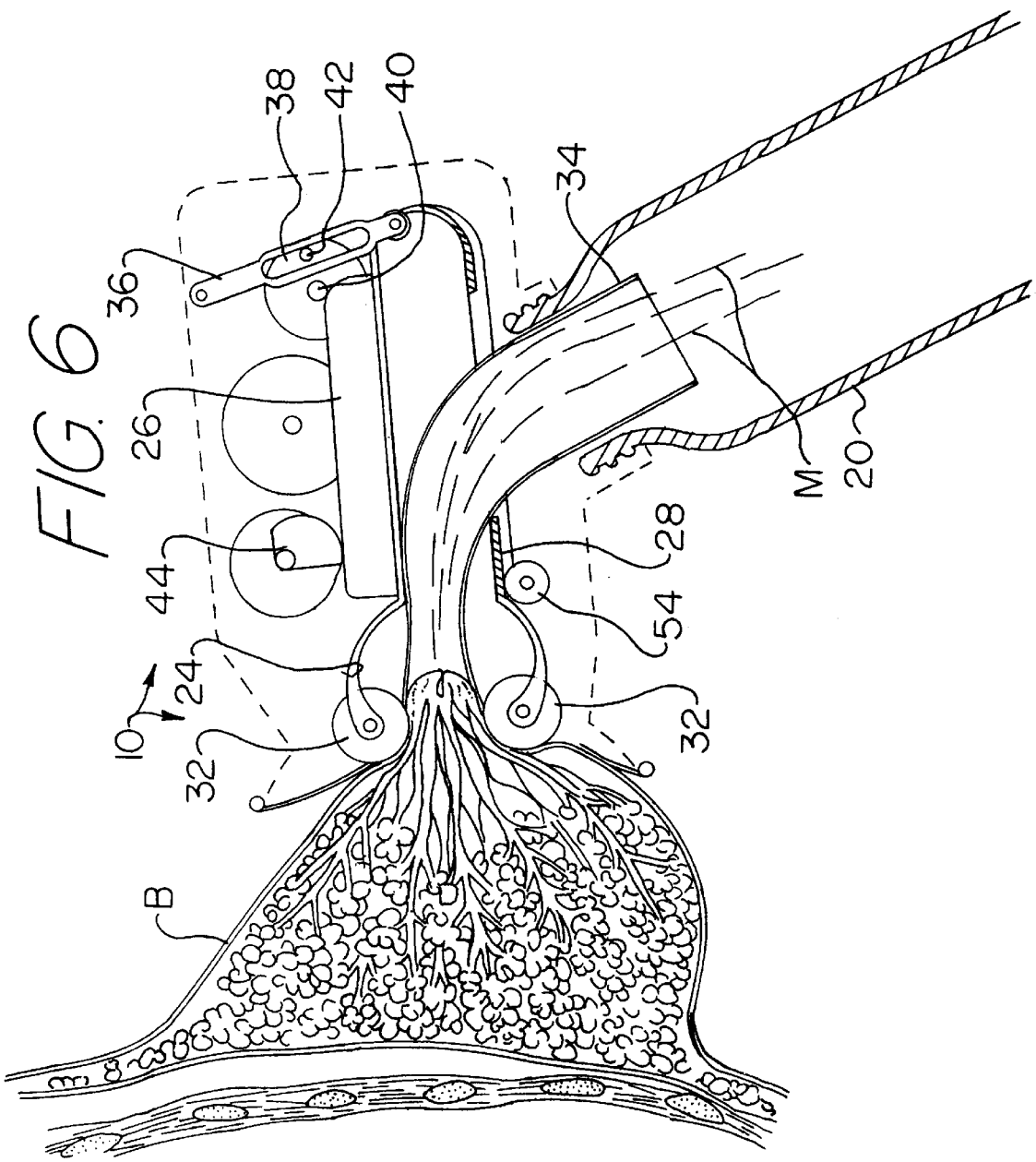
FIG. 6 is a sectioned view of the breast pump with the sleeve in a rearward squeezed position.

Referring now to the drawings, it is seen that the breast pump of the present invention, generally denoted by reference numeral 10, is comprised of a housing 12 having a first opening 14 and a second opening 16. The outer periphery of the first opening 14 has a padded element 18. A receptacle 20, for collecting the milk M, is removably secured to the housing 12 proximate the second opening 16. A plate 22 can be secured to the device for easy holding by a user. A flexible sleeve has a first side 24 having a flange 26, and a second side 28 having a third opening 30, and is disposed within the housing 12. The flexible sleeve is made from an appropriate flexible material such as spring metal, flexible plastic and the like. Located on one end of each of the first side 24 and the second side 28 is a roller 32. A tube 34 extends from proximate the first opening 14 through the second opening 16 and terminates either proximate the receptacle 20 or within the receptacle 20. The tube 34, which must also be flexible, is made from similar material from that which the flexible sleeve is made from.

A connection rod 36 has one end pivotally secured to the housing 12 and an opposing end pivotally secured to the flexible sleeve. A wheel 38, having a center 40, is rotatably disposed within the housing 12. A post 42 extends upward from the wheel 38 and is located in offset relation to the center 40. A cam 44, which may be round, or as illustrated flattened, is reciprocatively disposed within the housing 12 and engages the first side 24 of the sleeve by way of the flange 26. A motor assembly 46 operatively connects to the wheel 38 for providing rotational capability and to the cam 44 for providing reciprocating capability. The motor (not illustrated) of the motor assembly 46 may be powered in any desired fashion such as by way of a battery (not illustrated), which may be rechargeable, or by being plugged into a standard wall socket.

A control knob 48 is also operatively connected to the motor assembly 46 for manually providing rotational capability of the wheel 38 and reciprocating capability of the cam 44 independent of the motor. A control switch 50 provides on/off control for the motor while an adjustment switch 52 controls speed of the motor.

An adjustment system allows the initial distance between the first side 24 of the sleeve and the second side 28 of the sleeve to be adjusted. The adjustment system is comprised of a roller 54 that engages one of the sides 24 or 28. A spring 56 has one end biased against the roller 54 and the opposite end biased against an adjustment knob 58 that is rotatably connected to the housing 12. Rotation of the adjustment knob 58 increases the bias of the spring 56 and thus decreases the distance between the first side 24 of the sleeve and the second side 28 of the sleeve while counterrotation of the adjustment knob 58 decreases the bias of the spring 56 and thereby increases the distance between the first side 24 of the sleeve and the second side 28 of the sleeve.

In order to utilize the breast pump 10 of the present invention, the user attaches a receptacle 20 to the device 10 and uses the adjustment system to adjust the distance between the first side 24 of the sleeve and the second side 28 of the sleeve to comfortably fit the user's particular breast size. The user inserts her breast B into the housing 12 through the first opening 14. If desired, the control knob 48 can be rotates to insure that the initial parameters are suited for the user. Thereafter, the user uses the switch 50 to energize the motor and the adjustment switch 52 to set the speed of the motor.

In operation, the rotating wheel 38 causes the post 42 to act on the connection rod 36 causing the connection rod 36 to reciprocate the sleeve back and forth relative to the first opening 14, thereby impacting a pulling action on the breast B. The rollers 32 located on the sleeve assure that no undue discomfort or pain is occasioned on the user. The cam 44 acts to increase and decrease the distance between the first side 24 of the sleeve and the second side 28 of the sleeve, thereby impacting a squeezing action on the breast B. Using a generally round cam allows the first side 24 of the sleeve and the second side 28 of the sleeve to be squeezed and unsqueezed gradually, while a generally flattened cam 44 allows the first side 24 of the sleeve and the second side 28 of the sleeve to quickly squeeze and unsqueeze during the cycle. The combined pulling action and the squeezing action on the breast B causes the breast to be milked. The milk M flows through the tube 34 and is deposited within the receptacle 20. After the milking process is complete, the motor is deenergized and the breast B is removed from the housing 12.

While the invention has been particularly shown and described with reference to an embodiment thereof, it will be appreciated by those skilled in the art that various changes in form and detail may be made without departing from the spirit and scope of the invention.

We claim:

1. A breast pump comprising:
   a housing having a first opening;
   a flexible sleeve, having a first end and an open second end joined by a first side and a second side, the second side having a second opening, disposed within the housing proximate the first opening;
   a tube, having a third end proximate the second end and a fourth end, disposed within the housing and passing through the second opening;
   a reciprocating means for reciprocating the sleeve in a back and forth relation relative the first opening; and
   a squeezing means for squeezing and unsqueezing the sleeve.

2. The breast pump as in claim 1 wherein the squeezing means comprises:
   a motor; and
   a cam, reciprocatively disposed within the housing and engagable with the sleeve, operatively connected to the motor.

3. The breast pump as in claim 2 further comprising a flange attached to the first side such that the cam engages the sleeve via the flange.

4. The breast pump as in claim 1 wherein the reciprocating means comprises:
   a connection rod having a fifth end pivotally attached to housing, a sixth end pivotally attached to the first end, and a slotted portion;
   a motor;
   a wheel, having a center, rotatably disposed within the housing and operatively connected to the motor; and
   a post attached to the wheel in offset relation to the center and received within the slotted portion.

5. The breast pump as in claim 1 further comprising a receptacle attached to the housing and receiving the fourth end.

6. The breast pump as in claim 1 further comprising at least one roller attached to the second end.

7. The breast pump as in claim 1 further comprising:
   a first roller attached to the first side proximate the second end; and
   a second roller attached to the second side proximate the second end.

8. The breast pump as in claim 1 further comprising a padded member encompassing the first opening.

9. The breast pump as in claim 1 further comprising a roller disposed within the housing and biased between the housing and the second side.

10. The breast pump as in claim 1 further comprising:
    a roller disposed within the housing and engaging the second side;
    a knob rotatably disposed within the housing; and
    a spring having a fifth end biased against the roller and a sixth end biased against the knob such that rotation of the knob increases the bias of the spring and counter-rotation of the knob decreases the bias of the spring.

11. The breast pump as in claim 1 further comprising a switch for controlling operation of the motor.

12. A breast pump comprising:
    a housing having a first opening;
    a flexible sleeve, having a first end and an open second end and a first side and a second side, the second side having a second opening, disposed within the housing proximate the first opening;
    a tube, having a third end proximate the second end and a fourth end, disposed within the housing and passing through the second opening;
    a connection rod having a fifth end pivotally attached to housing, a sixth end pivotally attached to the flexible sleeve, and a slotted portion;
    a motor;
    a wheel, having a center, rotatably disposed within the housing and operatively connected to the motor;
    a post attached to the wheel in offset relation to the center and received within the slotted portion; and
    a cam, reciprocatively disposed within the housing and engagable with the sleeve, operatively connected to the motor.

13. The breast pump as in claim 12 further comprising a flange attached to the first side such that the cam engages the sleeve via the flange.

14. The breast pump as in claim 12 further comprising a receptacle attached to the housing and receiving the fourth end.

15. The breast pump as in claim 12 further comprising at least one roller attached to the second end.

16. The breast pump as in claim 12 further comprising:
    a first roller attached to the first side proximate the second end; and
    a second roller attached to the second side proximate the second end.

17. The breast pump as in claim 12 further comprising a padded member encompassing the first opening.

18. The breast pump as in claim 12 further comprising a roller disposed within the housing and biased between the housing and the second side.

19. The breast pump as in claim 12 further comprising:

a roller disposed within the housing and engaging the second side;

a knob rotatably disposed within the housing; and a spring having a seventh end biased against the roller and an eight end biased against the knob such that rotation of the knob increases the bias of the spring and counterrotation of the knob decreases the bias of the spring.

20. The breast pump as in claim 12 further comprising a switch for controlling operation of the motor.

\* \* \* \* \*